(12) United States Patent
Sherman et al.

(10) Patent No.: US 7,628,800 B2
(45) Date of Patent: Dec. 8, 2009

(54) FORMED IN PLACE CORPECTOMY DEVICE

(75) Inventors: Michael C. Sherman, Memphis, TN (US); Samuel M. Shaolian, Newport Beach, CA (US)

(73) Assignee: Warsaw Orthopedic, Inc.

( * ) Notice: Subject to any disclaimer, the term of this patent is extended or adjusted under 35 U.S.C. 154(b) by 61 days.

(21) Appl. No.: 11/145,238

(22) Filed: Jun. 3, 2005

(65) Prior Publication Data
US 2006/0293750 A1 Dec. 28, 2006

(51) Int. Cl.
*A61B 17/88* (2006.01)
(52) U.S. Cl. ................................ 606/279
(58) Field of Classification Search ............... 606/61, 606/72, 92–93, 246, 279, 86 R; 623/17.12
See application file for complete search history.

(56) References Cited

U.S. PATENT DOCUMENTS

| | | | |
|---|---|---|---|
| 2,267,925 A | 12/1941 | Johnston | |
| 3,834,394 A | 9/1974 | Hunter et al. | |
| 3,875,595 A | 4/1975 | Froning | |
| 4,041,939 A | 8/1977 | Hall | |
| 4,289,123 A | 9/1981 | Dunn | |
| 4,327,734 A | 5/1982 | White, Jr. | |

(Continued)

FOREIGN PATENT DOCUMENTS

DE 197 26 754 A1 2/1999

(Continued)

OTHER PUBLICATIONS

International Search Report for Application No. PCT/US2006/020887 (the PCT counterpart of the parent application) mailed Nov. 9, 2006.

(Continued)

*Primary Examiner*—Thomas C Barrett
*Assistant Examiner*—Michael J Araj

(57) ABSTRACT

An inflatable corpectomy device includes a balloon, which defines a cavity for receiving a hardenable media. The device can be inserted in an un-inflated form into a space formerly occupied by a diseased or damaged vertebrae bone. When inflated with a hardenable material, the device expands and fills the space. Various bone anchors or plates can be used in combination with the inflatable device to bridge the space and stabilize the spine while the device hardens.

11 Claims, 12 Drawing Sheets

U.S. PATENT DOCUMENTS

| | | | |
|---|---|---|---|
| 4,341,218 A | 7/1982 | Ü | |
| 4,364,392 A | 12/1982 | Strother et al. | |
| 4,383,879 A | 5/1983 | Le Du et al. | |
| 4,441,495 A | 4/1984 | Hicswa | |
| 4,517,979 A | 5/1985 | Pecenka | |
| 4,545,367 A | 10/1985 | Tucci | |
| 4,648,388 A | 3/1987 | Steffee | |
| 4,743,260 A | 5/1988 | Burton | |
| 4,772,287 A | 9/1988 | Ray et al. | |
| 4,887,595 A | 12/1989 | Heinig et al. | |
| 4,892,550 A | 1/1990 | Huebsch | |
| 4,904,260 A | 2/1990 | Ray et al. | |
| 4,998,936 A | 3/1991 | Mehdian | |
| 5,000,165 A | 3/1991 | Watanabe | |
| 5,030,220 A | 7/1991 | Howland | |
| 5,037,445 A | 8/1991 | Sander et al. | |
| 5,084,049 A | 1/1992 | Asher et al. | |
| 5,084,051 A | 1/1992 | Törmälä et al. | |
| 5,108,404 A | 4/1992 | Scholten et al. | |
| 5,139,499 A | 8/1992 | Small et al. | |
| 5,146,933 A | 9/1992 | Boyd | |
| 5,165,919 A | 11/1992 | Sasaki et al. | |
| 5,171,279 A | 12/1992 | Mathews | |
| 5,171,280 A | 12/1992 | Baumgartner | |
| 5,176,680 A | 1/1993 | Vignaud et al. | |
| 5,181,921 A | 1/1993 | Makita et al. | |
| 5,222,970 A | 6/1993 | Reeves | |
| 5,236,460 A | 8/1993 | Barber | |
| 5,242,443 A | 9/1993 | Kambin | |
| 5,242,444 A | 9/1993 | MacMillan | |
| 5,306,275 A | 4/1994 | Bryan | |
| 5,342,361 A | 8/1994 | Yuan et al. | |
| 5,357,983 A | 10/1994 | Mathews | |
| 5,395,372 A * | 3/1995 | Holt et al. | 606/86 B |
| 5,397,363 A | 3/1995 | Gelbard | |
| 5,464,407 A | 11/1995 | McGuire | |
| 5,470,336 A | 11/1995 | Ling et al. | |
| 5,474,551 A | 12/1995 | Finn et al. | |
| 5,484,418 A | 1/1996 | Quiachon et al. | |
| 5,486,174 A | 1/1996 | Fournet-Fayard et al. | |
| 5,496,322 A | 3/1996 | Mathews | |
| 5,520,689 A | 5/1996 | Schlapfer et al. | |
| 5,529,653 A | 6/1996 | Glastra | |
| 5,549,679 A | 8/1996 | Kuslich | |
| 5,556,429 A | 9/1996 | Felt | |
| 5,562,661 A | 10/1996 | Yoshimi et al. | |
| 5,562,736 A | 10/1996 | Ray et al. | |
| 5,569,248 A | 10/1996 | Mathews | |
| 5,571,189 A | 11/1996 | Kuslich | |
| 5,584,887 A | 12/1996 | Kambin | |
| 5,591,165 A | 1/1997 | Jackson | |
| 5,591,167 A | 1/1997 | Laurain et al. | |
| 5,591,199 A | 1/1997 | Porter et al. | |
| 5,593,408 A | 1/1997 | Gayet et al. | |
| 5,649,925 A | 7/1997 | Barbera Alacreu | |
| 5,658,286 A | 8/1997 | Sava | |
| 5,658,289 A | 8/1997 | Boucher | |
| 5,658,310 A * | 8/1997 | Berger | 606/192 |
| 5,720,751 A | 2/1998 | Jackson | |
| 5,728,097 A | 3/1998 | Mathews | |
| 5,733,260 A | 3/1998 | DeMaio et al. | |
| 5,752,955 A | 5/1998 | Errico | |
| 5,772,661 A | 6/1998 | Michelson | |
| 5,792,044 A | 8/1998 | Foley et al. | |
| 5,792,106 A | 8/1998 | Mische | |
| 5,795,353 A | 8/1998 | Felt | |
| 5,800,435 A | 9/1998 | Errico et al. | |
| 5,827,289 A | 10/1998 | Reiley et al. | |
| 5,840,059 A | 11/1998 | March et al. | |
| 5,879,713 A | 3/1999 | Roth et al. | |
| 5,888,220 A | 3/1999 | Felt et al. | |
| 5,899,939 A | 5/1999 | Boyce et al. | |
| 5,910,142 A | 6/1999 | Tatar | |
| 5,938,663 A | 8/1999 | Petreto | |
| 5,972,015 A | 10/1999 | Scribner et al. | |
| 5,980,253 A | 11/1999 | Oxman et al. | |
| 6,022,376 A * | 2/2000 | Assell et al. | 623/17.16 |
| 6,025,406 A | 2/2000 | Oxman et al. | |
| 6,033,406 A | 3/2000 | Mathews | |
| 6,042,380 A | 3/2000 | De Rowe | |
| 6,043,295 A | 3/2000 | Oxman et al. | |
| 6,048,343 A | 4/2000 | Mathis et al. | |
| 6,048,346 A | 4/2000 | Reiley et al. | |
| 6,066,154 A | 5/2000 | Reiley et al. | |
| 6,080,801 A | 6/2000 | Draenert et al. | |
| 6,099,528 A | 8/2000 | Saurat | |
| 6,102,912 A | 8/2000 | Cazin et al. | |
| 6,106,530 A | 8/2000 | Harada | |
| 6,123,707 A | 9/2000 | Wagner | |
| 6,126,689 A | 10/2000 | Brett | |
| 6,127,597 A | 10/2000 | Beyar et al. | |
| 6,149,655 A | 11/2000 | Constantz et al. | |
| 6,159,012 A | 12/2000 | Oxman et al. | |
| 6,175,758 B1 | 1/2001 | Kambin | |
| 6,176,882 B1 | 1/2001 | Biedermann et al. | |
| 6,206,922 B1 | 3/2001 | Zdeblick et al. | |
| 6,226,548 B1 | 5/2001 | Foley et al. | |
| 6,235,028 B1 | 5/2001 | Brumfield et al. | |
| 6,241,734 B1 | 6/2001 | Scribner et al. | |
| 6,248,110 B1 * | 6/2001 | Reiley et al. | 606/93 |
| 6,280,456 B1 | 8/2001 | Scribner | |
| 6,296,643 B1 | 10/2001 | Hopf et al. | |
| 6,296,644 B1 | 10/2001 | Saurat et al. | |
| 6,306,177 B1 | 10/2001 | Felt et al. | |
| 6,332,894 B1 | 12/2001 | Stalcup et al. | |
| 6,336,930 B1 | 1/2002 | Stalcup et al. | |
| 6,395,034 B1 | 5/2002 | Suddaby | |
| 6,402,784 B1 | 6/2002 | Wardlaw | |
| 6,425,923 B1 | 7/2002 | Stalcup et al. | |
| 6,443,988 B2 | 9/2002 | Felt et al. | |
| 6,447,514 B1 | 9/2002 | Stalcup | |
| 6,530,926 B1 | 3/2003 | Davison | |
| 6,530,929 B1 | 3/2003 | Justis et al. | |
| 6,558,386 B1 | 5/2003 | Cragg | |
| 6,558,390 B2 | 5/2003 | Cragg | |
| 6,632,235 B2 * | 10/2003 | Weikel et al. | 606/192 |
| 6,706,069 B2 * | 3/2004 | Berger | 623/17.12 |
| 6,726,691 B2 | 4/2004 | Osorio et al. | |
| 6,805,697 B1 * | 10/2004 | Helm et al. | 606/92 |
| 6,805,715 B2 * | 10/2004 | Reuter et al. | 623/17.12 |
| 6,866,682 B1 | 3/2005 | An et al. | |
| 7,226,481 B2 * | 6/2007 | Kuslich | 623/17.11 |
| 2001/0004710 A1 | 6/2001 | Felt et al. | |
| 2002/0022764 A1 | 2/2002 | Smith et al. | |
| 2002/0045904 A1 | 4/2002 | Fuss et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0082601 A1 | 6/2002 | Toyama et al. | |
| 2002/0120270 A1 * | 8/2002 | Trieu et al. | 606/61 |
| 2002/0161368 A1 | 10/2002 | Foley et al. | |
| 2002/0198526 A1 | 12/2002 | Shaolian et al. | |
| 2003/0028251 A1 * | 2/2003 | Mathews | 623/17.16 |
| 2003/0040800 A1 | 2/2003 | Li et al. | |
| 2003/0055430 A1 | 3/2003 | Kim | |
| 2003/0083749 A1 | 5/2003 | Kuslich et al. | |
| 2003/0144624 A1 | 7/2003 | Barbut | |
| 2003/0195547 A1 | 10/2003 | Scribner et al. | |
| 2004/0006341 A1 | 1/2004 | Shaolian et al. | |
| 2004/0158250 A1 | 8/2004 | Chappuis | |
| 2005/0010220 A1 | 1/2005 | Casutt et al. | |
| 2005/0010297 A1 * | 1/2005 | Watson et al. | 623/17.12 |
| 2005/0027358 A1 * | 2/2005 | Suddaby | 623/17.11 |

| | | | |
|---|---|---|---|
| 2005/0033430 A1* | 2/2005 | Powers et al. ............ 623/17.11 | |

| | | |
|---|---|---|
| WO | WO 00/44288 | 8/2000 |

FOREIGN PATENT DOCUMENTS

| | | |
|---|---|---|
| DE | 200 17 962 U1 | 1/2001 |
| SU | 839513 | 5/1981 |
| SU | 1 745 231 | 7/1992 |
| WO | WO 97/30666 | 8/1997 |
| WO | WO 97/38639 | 10/1997 |
| WO | WO 99/09902 | 3/1999 |
| WO | WO 99/15097 | 4/1999 |
| WO | WO 99/26549 | 6/1999 |

OTHER PUBLICATIONS

Bennett, Gregory J., "Lumbosacral Stabilization Using Screw Fixation Techniques," *Neurosurgery*, 2nd Edition, vol. 2, McGraw-Hill Health Professions Division, pp. 3027-3035.

Müller, Adolf, M.D. et al. A Keyhole Approach for Endoscopically Assisted Pedicle Screw Fixation in Lumbar Spine Instability, *Neurosurgery*, vol. 47, No. 1, Jul. 2000, pp. 85-96.

International Search report for European Application No. 00 98 9371 (The European counterpart of the parent application) mailed Jan. 2, 2007.

* cited by examiner

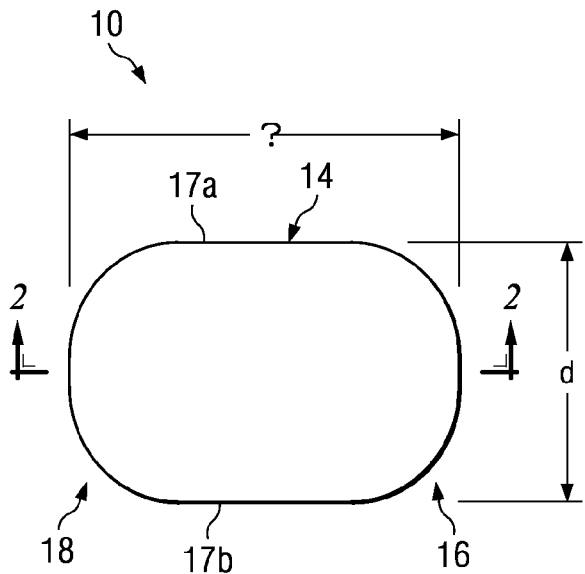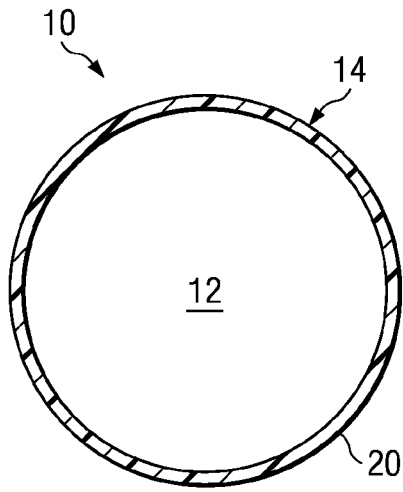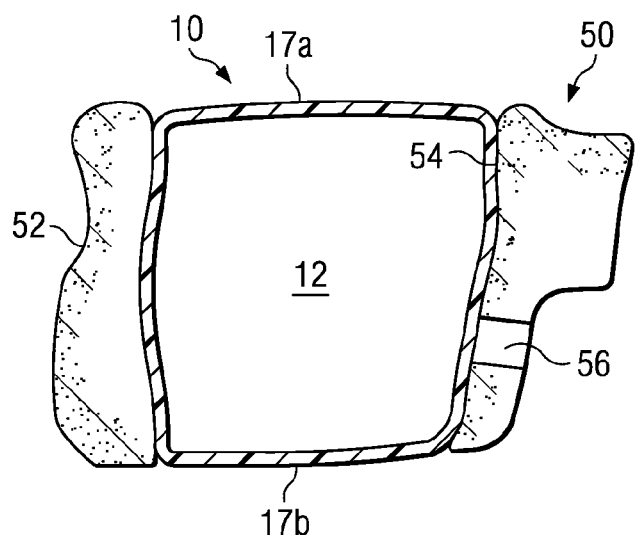

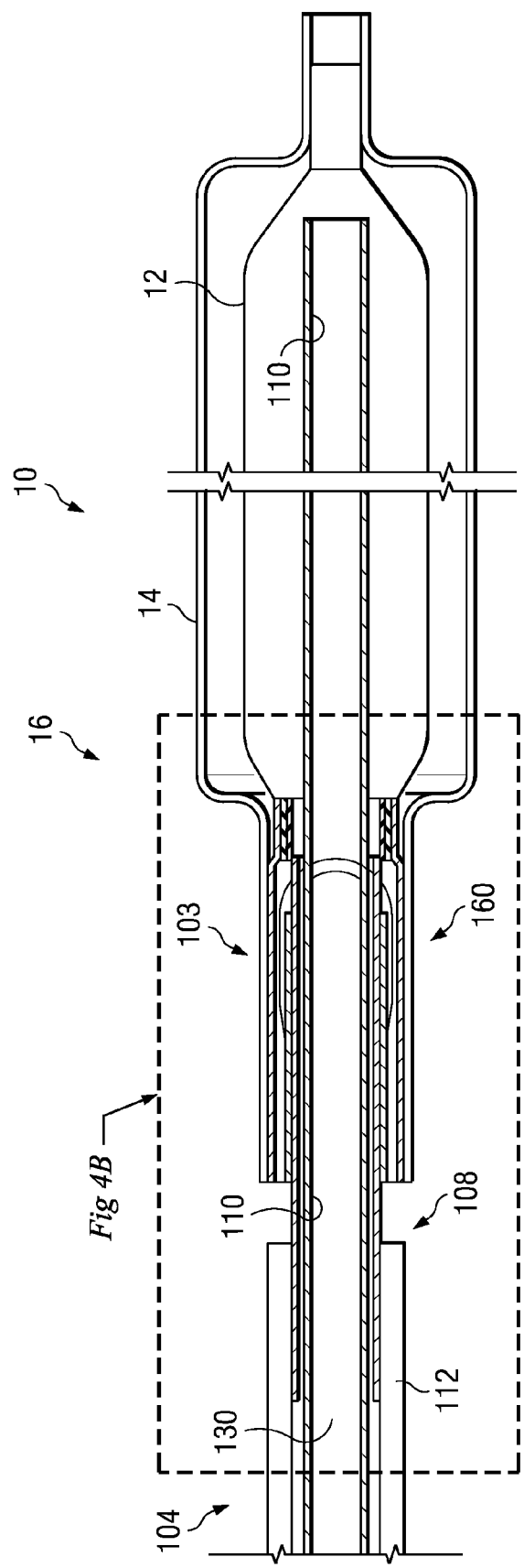

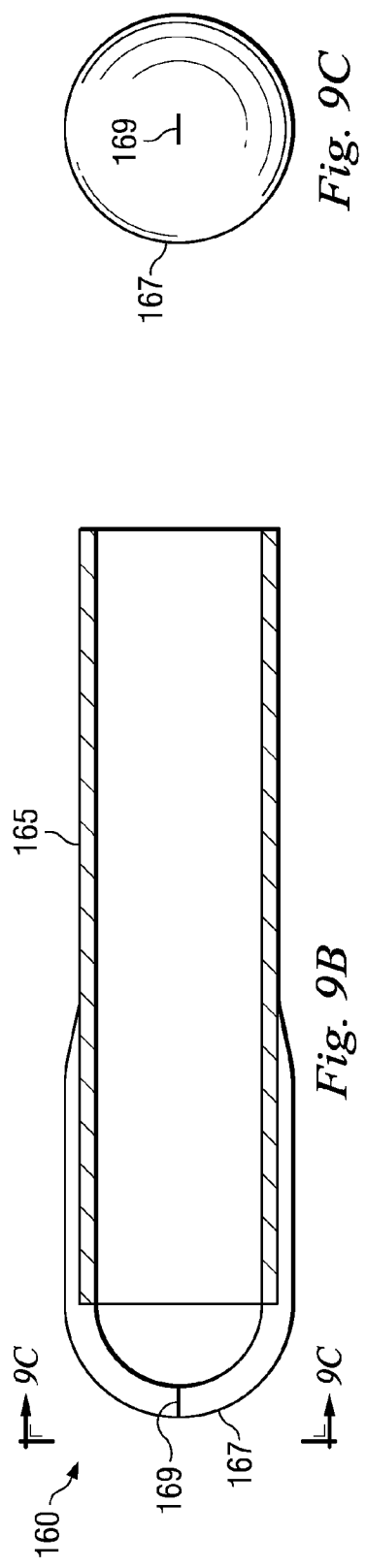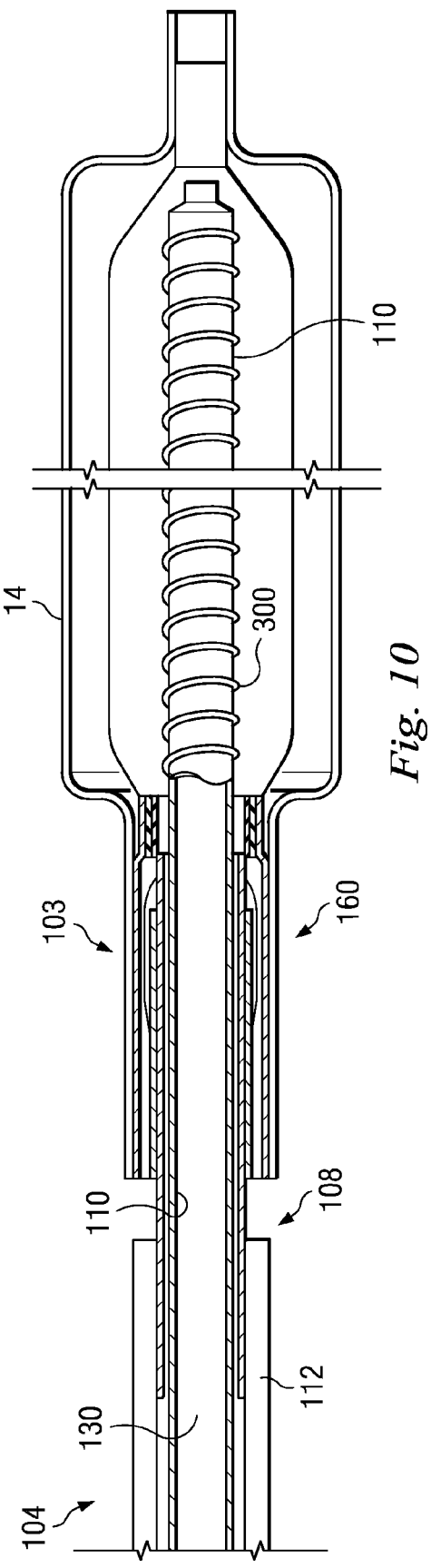

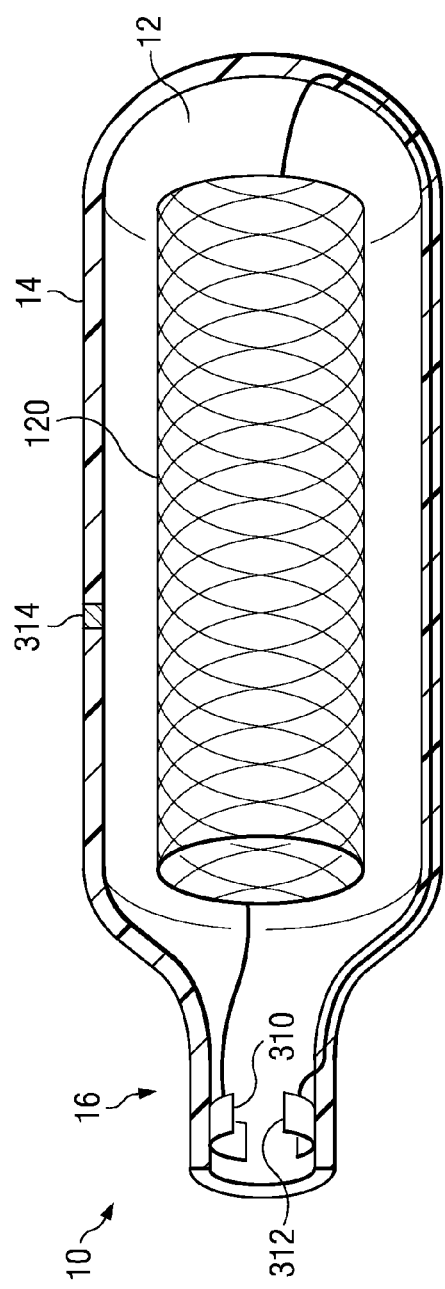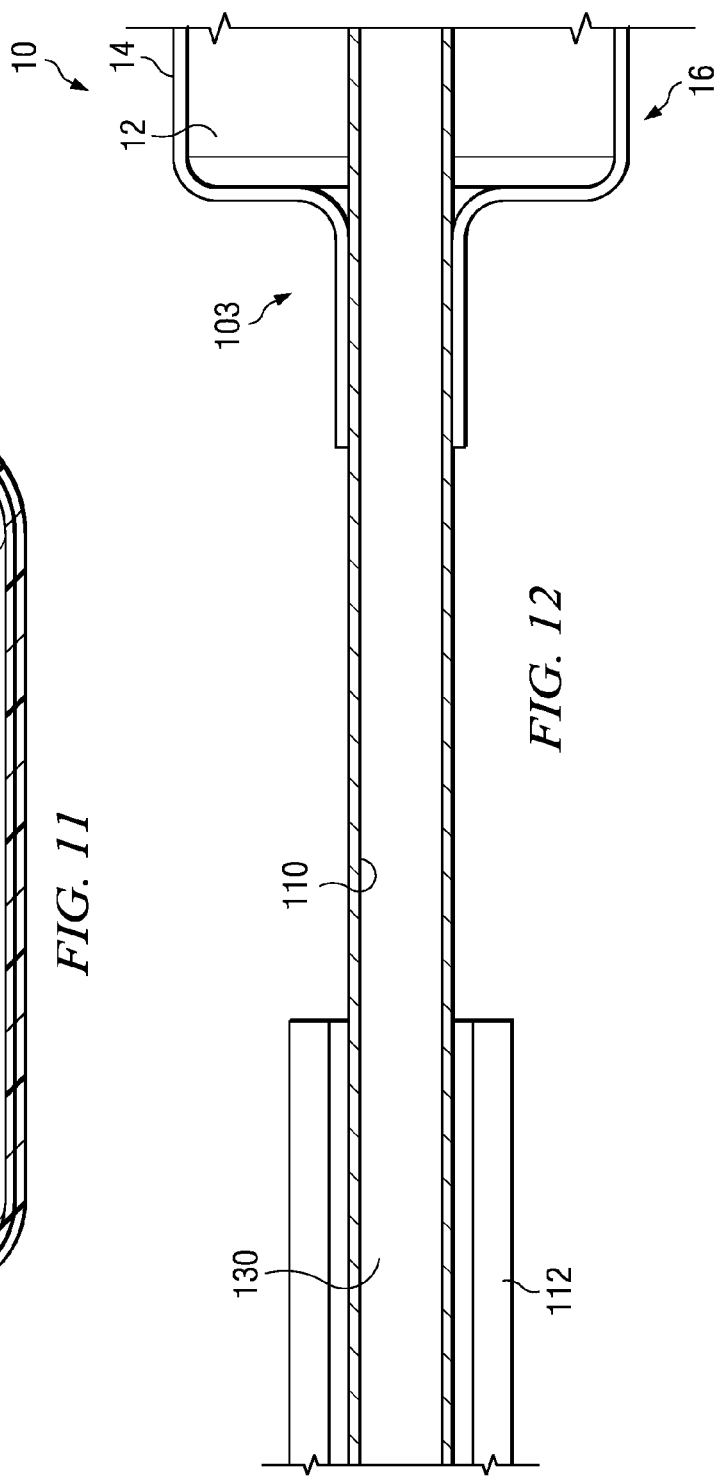

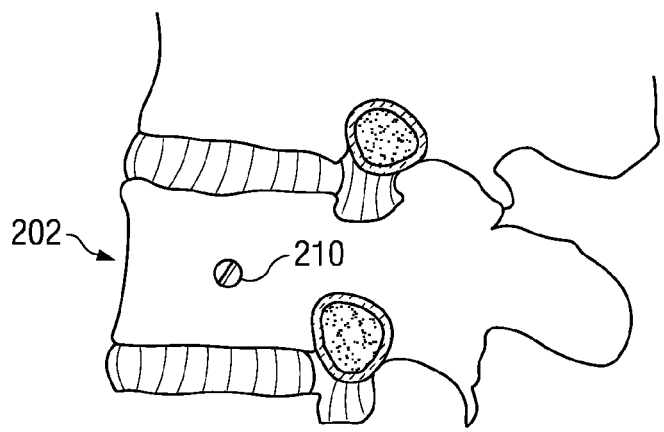
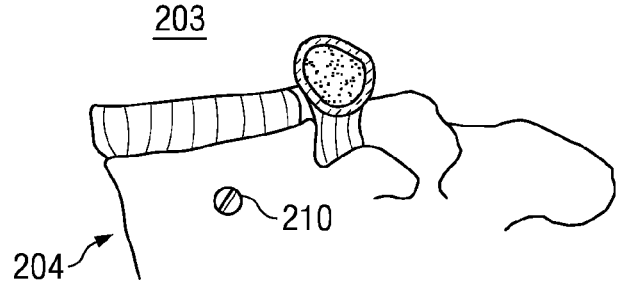
Fig. 15
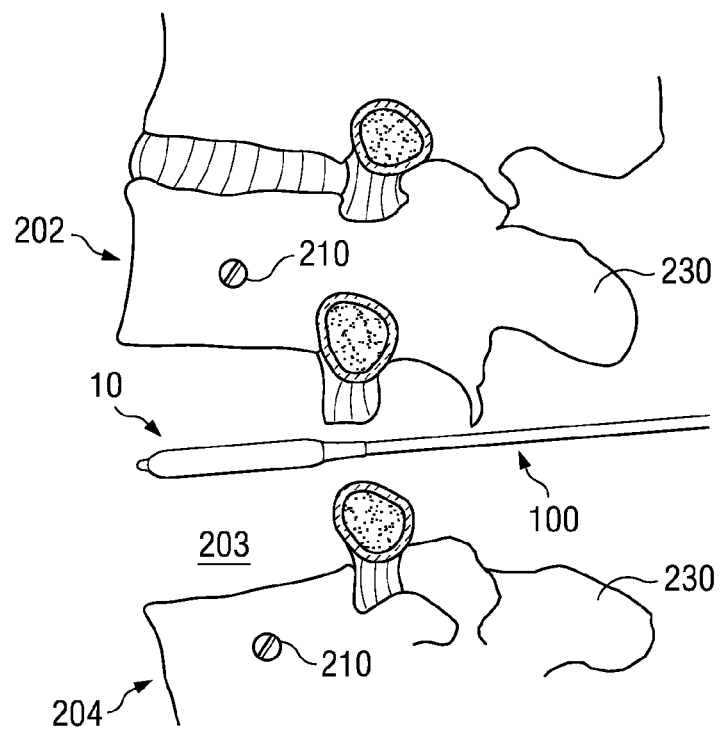
Fig. 16

FORMED IN PLACE CORPECTOMY DEVICE

BACKGROUND OF THE INVENTION

1. Field of the Invention

The present invention relates to medical devices and techniques and, more particularly, to systems and methods for treating injuries, deformities or diseases of the spine.

2. Description of the Related Art

Corpectomy is a well-known procedure that is performed to relive the pain caused by a diseased (e.g., with a tumor) or damaged (e.g., fractured) vertebrae bone that blocks and pinches the spinal cord. It can also be used as part of a strategy to correct spinal column deformities.

Often, corpectomies involve making an incision into the patient to expose the diseased or damaged portion of the vertebrae bone. The diseased or damaged parts of the vertebrae bone are then removed to relieve pressure from the spinal cord. The disc levels below and above the removed vertebrae bone along with any diseased fragments are also removed. The bone surfaces are then cleared and prepared to receive a bone graft or a corpectomy device (see e.g., U.S. Pat. No. 6,866,682). Fixation devices (e.g., screws) are inserted into the vertebrae below and above the gap. The fixation devices are used to decompress the vertebrae space and/or correct the spinal column curvature. The surgeon then inserts the bone graft into the gap, closing the space between the upper and lower vertebrae bones. A plate (e.g., a "Z-plate") bridges the gap filled by the graft and is coupled to the fixation devices in the upper and lower vertebrae bones. The plate secures the area while the upper and lower vertebrae bones fuse to the bone graft to create one solid bone segment.

While corpectomy is a proven procedure used to address certain spinal diseases, injuries and defects; it does suffer from several drawbacks. For example, it is associated with morbidity, high costs, lengthy in-patient hospital stays and the pain associated with open surgical procedures. Therefore, there is a need for devices and methods for performing a corpectomy, which cause less pain and potential complications. Preferably, the devices and methods utilize minimally invasive procedures.

SUMMARY OF THE INVENTION

There is provided in accordance with one embodiment of the present invention a method of treating the spine that includes removing a damaged or diseased portion of the spine to create a space at a treatment site. An inflatable balloon is positioned into the space. A curable media is injected into the balloon, which expands to at least partially fill the space. The curable media is allowed to cure within the body.

Another embodiment of the present invention comprises a corpectomy prosthesis that includes a balloon having an inflated shape configured to fill a gap between a first vertebrae bone and a second non-adjacent vertebrae bone that is created during a corpectomy procedure. The prosthesis also includes a hardenable media that is positioned within the balloon and is configured to harden while the balloon is positioned within the body of a patient.

Another embodiment of the present invention comprises a kit for use in a corpectomy procedure. The kit includes a balloon having an inflated shape configured to fill a gap in a vertebral column created by the corpectomy procedure. A hardenable media for injecting within the balloon. The media is configured to harden while the balloon is positioned within the gap. The kit also includes a deployment catheter configured to deliver the balloon and hardenable media to the gap.

BRIEF DESCRIPTION OF THE DRAWINGS

FIG. 1 is a side elevation view of an exemplary embodiment of an inflatable corpectomy device.

FIG. 2 is a cross-sectional view taken through line 2-2 of FIG. 1.

FIG. 3 is a cross-sectional view taken through a bone graft and a modified embodiment of an inflatable corpectomy device.

FIG. 4A is a side elevational cross section of a distal portion of the delivery catheter of FIG. 4.

FIG. 9B is a schematic cross-sectional view of another embodiment of a valve.

FIG. 9C is an end view of the valve of FIG. 9B.

FIG. 10 is a schematic side elevational view of the distal end of a deployment catheter having a heated implant removably positioned thereon.

FIG. 11 is a schematic side elevational view an implant with a modified heating element.

FIG. 12 is a cross-sectional side view of the distal end of a modified embodiment of a deployment catheter having an implant thereon.

FIGS. 13-18 are partial cross-sectional midline sagittal views of a portion of a vertebral column showing an implantation method according to an embodiment of the present invention.

DETAILED DESCRIPTION OF THE PREFERRED EMBODIMENTS

Figure 4:
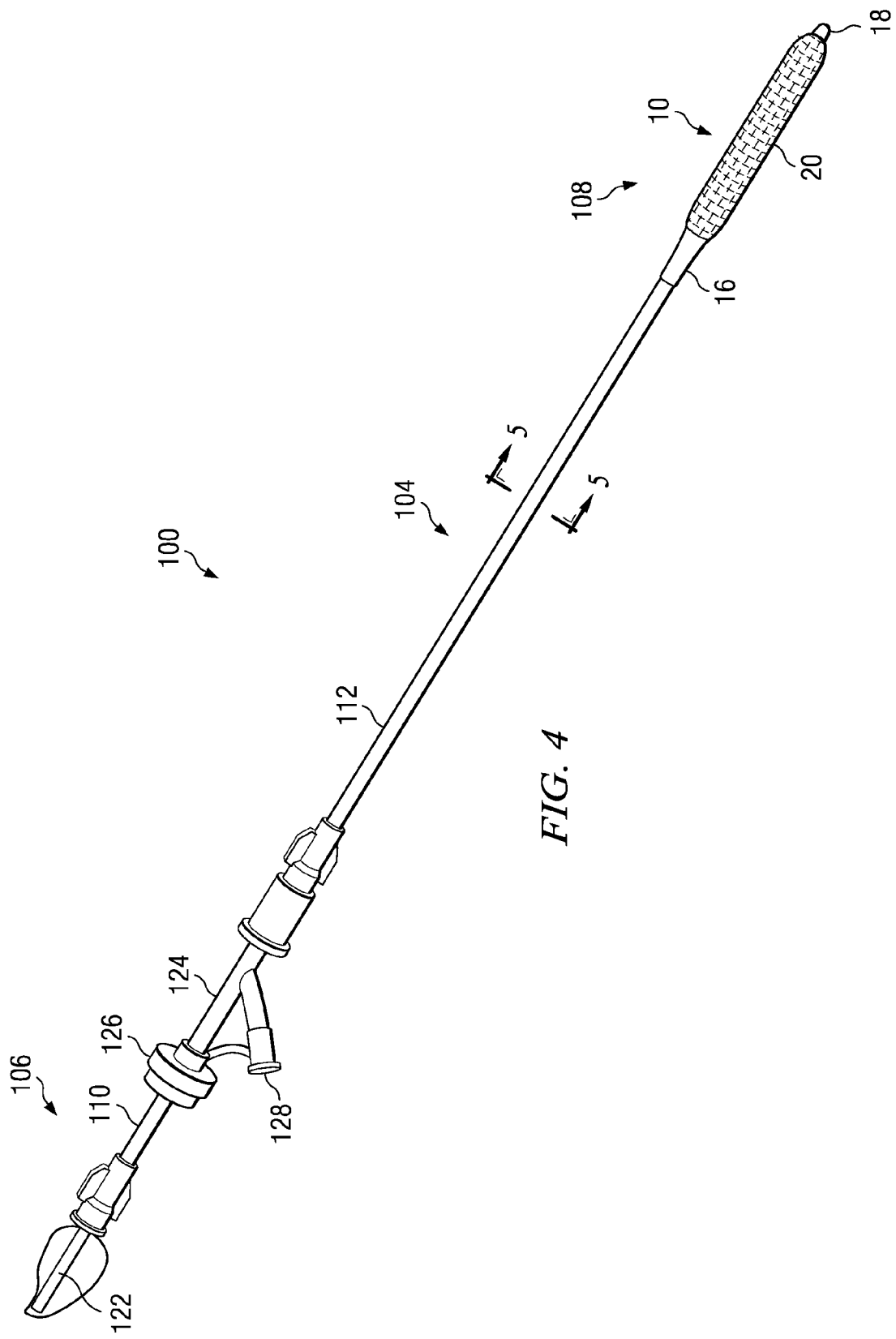
FIG. 4 is a side view of an exemplary embodiment of a delivery catheter having an inflatable corpectomy device thereon.

Although the application of the present invention will be disclosed primarily in connection with a specific spinal fixation procedure (i.e., corpectomy), the methods and devices disclosed herein are intended for use in any of a wide variety of medical applications where formation of an attachment, bulking, support, fixation or other element in situ may be desirable.

One advantage of the in situ prosthesis formation described herein is the ability to obtain access to a treatment site through a minimally invasive access pathway, while enabling the formation of a relatively larger implant at the treatment site. This allows procedure morbidity to be minimized, since open surgical cutdowns or other invasive access procedures may be avoided or minimized. In addition, the in situ formation in accordance with the certain embodiments described herein allows the formation of a corpectomy device having any of a wide variety of customized or predetermined shapes, due to the ability of the infusible hardenable media to assume the shape of the cavity or flexible container into which it is infused.

The methods and devices of certain embodiments described herein additionally enable access to a treatment site within the body along a curved and even tortuous pathway, through which a preformed prosthesis would not fit or would not be navigable. The inflatable corpectomy prosthesis of certain embodiments can be removably coupled to the distal end of an elongate flexible tubular catheter body, which can be dimensioned for percutaneous, surgical or transluminal advancement and deployment of an inflatable or otherwise curable in place prosthesis in any of a wide variety of orthopedic applications, such as the spine as disclosed in greater detail below, as well as long bones, short bones, and associated ligaments and tendons. In addition, the deployment catheter and prosthesis can be dimensioned for transluminal navigation throughout the cardiovascular system, the gastrointestinal tract, the biliary tract, the genitourinary tract, or the respiratory tract (e.g. the tracheobronchial tree). The device may thus be advanced through artificial access pathways as well as naturally occurring lumens and hollow organs. Additional applications of the in situ device formation technology disclosed herein will become apparent to those of skill in the art in view of the disclosure herein.

In connection with corpectomies, certain embodiments involve the partial or total removal of a diseased or damaged vertebrae bone. An implantable, inflatable orthopedic device is inserted using an anterior, posterior or lateral approach and inflated into the space formerly occupied by the removed vertebral bone or removed portions of bone. The inflatable orthopedic device can be inserted using open, minimally open or percutaneous techniques. In one embodiment, the device is inserted into the space using a transpedicle approach in which a deployment catheter is advanced through a pedicle of an adjacent vertebrae bone. Various bone anchors or plates can be used in combination with the inflatable device to bridge the space and stabilize the spine while the device or a graft fuses with the adjacent vertebrae bones. In a preferred embodiment, a deployment system, comprising a delivery catheter removably carrying the implantable device, is provided, such that at least portions of the procedure may be conducted in a percutaneous or minimally invasive manner to minimize procedure trauma to the patient.

With reference now to the illustrated embodiment, FIGS. 1 and 2 are side and cross-sectional views of an embodiment of an implantable orthopedic device 10, which can be used as an inflatable or formed in place corpectomy device. As will be explained below, the implantable device 10 can be removably carried by the distal end of a deployment catheter. The inflatable device 10 can also be used with a bone graft as will be explained below with reference to FIG. 3.

The implantable device 10 comprises a shell or balloon 14, which is shown in an inflated position in FIGS. 1 and 2. The balloon includes a proximal end 16, a distal end 18, and a flexible wall 20, which defines a cavity 12. Between the proximal and distal ends 16, 18, the balloon 14 has sides 17a, 17b, which, in the illustrated embodiment, form the upper and lower ends 17a, 17b of the device 10 when it is implanted into the patient as described below.

The balloon 14 may be formed from any of a variety of polymeric materials that are known in the balloon angioplasty arts. These include, for example, complaint materials such as polyethylene, polyethylene blends or nylon, and substantially noncompliant materials such as polyethylene terephthalate. Any of a wide variety of other biocompatible polymers may be utilized, as will be apparent to those of skill in the art in view of the disclosure herein.

The balloon 14 may comprise a single or multiple layers, depending upon the desired physical properties. In one embodiment, the balloon 14 comprises two layers, having a reinforcing structure such as a stent or a plurality of axially extending support strips sandwiched therebetween. In an alternate embodiment, the balloon 14 comprises a first, inner layer which restrains the hardenable media. A second, outer layer is coaxially disposed about the first layer, and is provided with a plurality of apertures or a microporous structure. An infusion lumen is provided in the delivery device for providing communication between a proximal infusion port and the space in between the inner and outer balloon layers. In this manner, fluids, which may contain any of a variety of medications or agents (e.g., orthobiologics and/or bone matrix material), can be infused into the tissue surrounding the treatment site. Suitable structures and manufacturing considerations are disclosed in U.S. Pat. No. 5,295,962 to Crocker et al., the disclosure of which is incorporated in its entirety herein by reference.

Although a generally cylindrical or disk-like configuration for the balloon 14 is illustrated herein, any of a variety of alternative cross sectional configurations may be utilized. The overall length, diameter and wall thickness of the implantable inflatable orthopedic device 10 can be varied, depending on the particular treatment and access site. In one embodiment, device 10 has an inflated diameter (d) or height between about 20 mm and about 30 mm and for positioning between two adjacent vertebrae. The device 10 has an inflated length (l) of generally between about 20 mm and 40 mm.

The diameter (d) or height of the balloon 14 is based upon the anticipated distance between the upper and lower vertebrae bones that define the boundaries of the space created by the corpectomy, or, in an embodiment in which only a portion of a vertebral body is replaced, the anticipated size of the space to be occupied by the device 10. For example, in an application a lumbar vertebrae is replaced (e.g. L4), the space between the upper and lower vertebrae will have distance within the range of from about 10 mm to about 15 mm. Preferably, the diameter of the balloon 14 is sufficiently large enough to occupy this space.

In other embodiments, the device 10 is configured to occupy the space of two or more adjacent replaced vertebrae. In such an embodiment, a device 10 configured to replace two vertebrae has an inflated diameter (d) or height between about 20 mm and about 40 mm, for positioning between two adjacent vertebrae. The device 10 has an inflated length (l) of generally between about 20 mm and about 40 mm.

It should be appreciated that the diameter (d) and length (l) of the device 10 described above are made with reference to an embodiment in which a deployment system is connected to the proximal end 16 of the device 10. However, it should be appreciated that this configuration represents just one exemplary embodiment of the device 10. It is anticipated that in modified embodiments the proximal and distal ends 16, 18 can correspond to the upper and lower ends 17a, 17b, when the device 10 is positioned within the patient. In other embodiments, the connection between the device 10 and the deployment system can be made at an angle with respect to a longitudinal axis of the spine.

The primary function of the balloon 14 is to influence or control the shape of a hardenable media injected therein. The implantable balloon 14 is not normally required to restrain pressure over an extended period of time. Thus, greater design flexibility may be permitted, compared to conventional angioplasty or other dilatation balloons. For example, the balloon 14 may be porous, either for drug delivery as has been discussed, or to permit osteoincorporation and/or soft tissue ingrowth.

Certain hardenable media which may be utilized in connection with the embodiments described herein, such as PMMA, have a significantly greater viscosity in the precured form, compared to conventional angioplasty balloon inflation media. In addition, since the balloon 14 is not intended to contain significant pressure, conventional high strength materials such as for high pressure angioplasty may not be necessary. This allows the balloon 14 to be constructed in any of a variety of ways, including techniques utilized for balloon angioplasty applications. In addition, the balloon 14 (or balloon-like structure) may be made out of any of a wide variety of woven or nonwoven fibers, fabrics, metal mesh such as woven or braided wires, and carbon. Biocompatible fabrics or sheet material such as ePTFE and Dacron® may also be used.

The hardenable media is preferably a rapid setting, liquid polymer or polymer precursor, such as polymethyl methacrylate (PMMA). However, any of a variety of other materials which provide the required stiffening or setting characteristics may be used, including any of a variety of epoxies, polyurethane, polyester or blends of polyurethane-silicone. Additional descriptions and embodiments of such materials can be found in U.S. Pat. No. 6,875,212, the entire contents of which are hereby incorporated by reference herein.

In the context of a rod or disc-shaped inflatable container, for use in the spinal fixation procedures described herein, the physical requirements of the hardenable media will depend upon the length and diameter of the rod as well as the physical requirements imposed by the implantation site. For certain embodiments, polymethyl methacrylate, epoxy, polyurethane or other particular material may or may not exhibit sufficient physical properties. Physical properties of hardenable materials can be modified through the addition of any of a variety of additives, such as carbon fibers, Kevlar or Titanium Rods, woven or laser etched metallic tubular stents, or other strength enhancers as will be understood in the art. The selection of a particular hardenable media, as well as the desirability of adding strength, flexibility, or other physical property enhancers, can be optimized for any particular implantation system through routine experimentation by those of skill in the art in view of the disclosure herein.

Certain composite materials, such as carbon fibers embedded in a bonding agent such as a two part epoxy, or two part polyurethane have been found particularly useful in forming the implant of the present invention. For example, graphite (carbon fibers) having a diameter within the range of from about 0.003 to about 0.007 inches are provided in bundles (tows) composed of from about 3,000 to about 12,000 fibers. One typical fiber useful for this purpose is manufactured by Hexcel Carbon Fibers, Salt Lake City, Utah, Part No. HS/CP-5000/IM7-GP 12K. Preferably, the Tow tensile strength is in the range of from about 5,000 to about 7,000 Mpa. Tow tensile modulus is within the range of from about 250 to about 350 Gpa.

In general, the composite rods in accordance with embodiment described herein will exhibit a static compression bending values (per ASTM F1717) within the range of from about 100 to about 200 lbs., and, preferably greater than about 150 lbs. The composite rods will exhibit a static torsion (per ASTM F1717) within the range of from about 300 to about 500 inch pounds, and, generally in excess of about 400 inch pounds. The rods will preferably reach at least about 5 million cycles, at 5 Hz. Each of these parameters may be measured in accordance with the protocols described in the American Society for Testing and Materials (ASTM) designation F1717-96.

Within the range of from about 30 to about 60 bundles of the carbon fiber described above is packed in a deflated balloon, optionally along with a Ni—Ti stent having an appropriate diameter and appropriate length to fit within the deflated balloon. Although any of a variety of stents may be utilized, one useful structure is similar to the Smart Stent (Cordis), which helps keep the structure intact and also adds structural strength to the implanted structure.

A one or a two part epoxy having a viscosity in the range of from about 100 to about 500 cps is then injected into the balloon under pressure such as by using a pump and pressure within the range of from about 4 ATM to about 10 ATM or more depending upon viscosity, balloon strength and other design considerations. The pump is run for a sufficient duration and under a sufficient pressure to ensure that the epoxy wets all of the fibers. This may range from about 10 minutes or more to about an hour, and, in one application where the pump was run at about 5 ATM pressure, requires at least about ½ hour. Specific method parameters may be optimized depending upon the viscosity of the epoxy, infusion pressure, infusion flow rate, density of the packed carbon fibers, and other variables as will be apparent to those of skill in the art in view of the disclosure herein.

In an alternate embodiment, carbon fibers having within the range of from about 15 to about 45 degrees of braids are utilized. The braid may be in the form of a plain weave, and may be obtained, for example, from Composite Structures Technology (Tehachapi, Calif.). A 0.5 inch diameter of 45 degrees braided carbon fiber sleeve is positioned within the center of the balloon. This braided sleeve conforms dimensionally to the inside diameter of the balloon. A 0.3 inch diameter braided carbon sleeve (again 45°×45° plain weave) may also be positioned concentrically within the balloon, within the outer braided carbon fiber sleeve. Unidirectional fibers are thereafter introduced inside of the ID of the inner braided carbon sleeve. Unidirectional fibers are also introduced into the annular gap between the two braided sleeves. The volume of the fiber per volume of balloon is generally within the range of from about 40% to about 55%. After placement of the foregoing structure within the spine, the epoxy mix having a viscosity within the range of from about 100 to about 500 cps is injected under 10 atmospheres pressure into the balloon.

Although the foregoing composite structure was described using a carbon fiber example, any of a variety of fibers may be positioned within the balloon to enhance the physical properties of the finished product. For example, Kevlar fibers, PEEK, and any of a variety of alternatives may be used. In general, the fibers will preferably provide a very high tensile strength and high modulus, having a low diameter to enhance deliverability of the device.

The use of braided sleeves will produce higher structural resistance to sheer stress as a result of torsional loads, plus the ability to distribute unidirectional fibers in a homogenous manner within the balloon at all times. This appears to improve the performance of the implant.

Any of a variety of alternate constructions can be readily utilized, in accordance with the teachings herein. For example, three or more tubular support tubes may be utilized. The layering sequence of the various components may be changed, and other features added or deleted depending upon the desired performance of the finished device. In addition, although the balloon 14 in one embodiment comprises a nylon single layer balloon, other materials may be utilized. In addition, multiple layer balloons may be utilized, with or without support structures such as stents, wires, or woven tubular support structures sandwiched therebetween.

In certain embodiments, it is desirable that the cured device 10 exhibit a particular modulus of elasticity. Such an embodiment advantageously provides for limited a degree of motion (e.g., side-side movement, compression, extension, and/or torsion), when the device is positioned within the patient. In this manner, at least some degree of the natural motion of the spine can be preserved after the device 10 fuses with the remaining portions of the spine. In one embodiment, the cured device 10 has a modulus of elasticity between about 10 to about 200 GPa.

Marker bands made of materials such as gold, platinum or tantalum may also be positioned on the balloon, to facilitate fluoroscopic visualization. Alternatively, a radio opaque material, such as tantalum powder, may be sprinkled among the carbon fibers prior to infusion of the epoxy or other hardenable media, to allow visualization during placement.

The epoxy or the polyurethane material preferably has a relatively fast cure rate at 37° C. A low viscosity (no greater than from about 100 to about 1000 CPS) facilitates rapid transluminal introduction through the delivery catheter and wetting of the relatively small interstitial spaces between adjacent carbon fibers. In addition, the polymer is preferably radiopaque. The polymerization is preferably minimally exothermic, to minimize or prevent thermal damage to the surrounding tissue. One epoxy which may be useful in the present invention is Epotek 301 available from Epoxy Technologies. This epoxy reaches 50 to 60% of its strength within about three to four hours following deployment, at 37° C. Using a bonding agent having these approximate characteristics, the patient can be restrained from rolling for an initial cure period of approximately three or four hours to achieve a partial cure (e.g., at least about 50% and preferably 60% or more), and be maintained in bed for a secondary cure period such as approximately the next eight to twelve hours or more to accommodate a full cure. Other formulations of two part epoxies or polyurethanes with faster cure times (preferably no more than about one hour full cure) can be formulated by changing the ratios of components and formulations for the catalysts. Cure time can also be accelerated through the use of accelerators, such as catalysts or the application of heat or other energy source as is discussed in detail below.

Terms such as "hardenable" or "curable" media are used interchangeably herein, and are intended to include any material which can be transluminally introduced through the catheter body into the cavity 12 while in a first, flowable form, and transitionable into a second, hardened form. These terms are intended to cover materials regardless of the mechanism of hardening. As will be understood by those of skill in the art, a variety of hardening mechanisms may exist, depending upon media selection, including UV, other wavelength of electromagnetic energy, or catalyst initiated polymerization, thermally initiated polymerization, solvent volatilization, and the like. While the media selection may affect catheter design in manners well understood by those of skill in the art, such as to accommodate outgasing of byproducts, application of heat, catalysts, or other initiating or accelerating influences, these variations do not depart from the concept of the invention of introducing a flowable media into a shape and subsequently curing the media to the shape. Two part medias, such as a two part epoxy or polyurethane, or a monomer and an initiator may be introduced into the cavity 12 through separate lumen extending throughout the tubular body. Expandable media may also be provided, such as a material which is implantable in a first, reduced volume, and which is subsequently enlargeable to a second, enlarged volume such as by the application of water or heat, or the removal of a restraint.

Various safety features to minimize the risk of rupture or leakage of the hardenable media may be utilized, depending upon design preferences. For example, a two-layer or three-layer or more balloon may be utilized to reduce the risk of rupture. In addition, the material of the single or multiple layers of the balloon may be selected to minimize escape of volatile components from the curable media. In one embodiment, a double balloon is provided having a nylon inner layer and a PET outer layer.

In addition, the inflation pressure of the curable media may be affected by the nature of the balloon 14. For example, a polyethylene balloon having a wall thickness of about 0.001" may have a burst pressure of about 7 to 8 atmospheres. In that embodiment, an inflation pressure of no more than about 4 to 5 atmospheres may be desired. A slightly higher inflation pressure, such as on the order of from about 5 to about 6 atmospheres, may be utilized with a nylon balloon. Relatively noncompliant materials such as PET have much higher burst pressures (range of 10-20 atmospheres), as is well understood in the balloon angioplasty arts.

In addition, the balloon contains a proximal valve as will be discussed in additional detail below. Multiple valves may be utilized, in series along the flow path, to reduce the risk of failure and escape of hardenable media. As a further safety feature, the deployment catheter may be provided with an outer spill sheath in the form of an elongate flexible tubular body which surrounds the deployment catheter and at least a proximal portion of the balloon. This spill sheath provides an additional removable barrier between the junction of the catheter and the balloon, and the patient. If a spill occurs during the filling process, the spill sheath will retain any escaped hardenable media, and the entire assembly can be proximally retracted from the patient. Following a successful filling of the balloon, the spill sheath and deployment catheter can be proximally retracted from the patient, leaving the inflated formable orthopedic fixation structure in place.

FIG. 3 is a cross-sectional midline sagittal view of a bone graft 50 that can be used in combination with the inflatable device 10 described above. The graft 50 can comprise autograft bone (i.e., a patient's own bone) that is, for example, harvested from the iliac crest (hip), an allograft bone (i.e., donor bone from a cadaver), which eliminates the need to harvest the patient's own bone or another type of artificial or natural rigid prosthesis inserted into the space created by the corpectomy. The graft 50 includes an outer surface 52 which is sized and configured generally to fit within the space created by the corpectomy as the diseased or damaged vertebral body or portion thereof is removed. In a modified embodiment, the graft 50 can be configured to fit within a portion of a vertebrae bone that has been removed.

Within the outer surface, the graft 50 includes inner surface 54, which is defines a bore configured to receive the inflatable device 10 described above. A channel or opening 56 can extend from the outer surface 52 to the inner surface 54 such that a delivery catheter (as will be described in more detail below) can be used to insert and inflate the device within the inner surface 54. The opening 56 can be preformed into the graft 50 or created in situ. Once inflated, the device 10 occupies the cavity defined by the inner space 54 providing the graft 50 with additional strength and density.

In a modified embodiment, the graft 50 and inner surface 54 define a cavity configured to receive a hardenable or curable media without the use of a balloon. That is, the graft itself constrains the hardenable or curable media and the media is injected directly into the graft 50. In yet another embodiment, the graft 50 and device 10 are coupled and inserted together into the patient. An injection device is then used to inflate the device 10.

The device 10 may be used in combination with various medicines and agents. In particular, it can be advantageous to use the device 10 in combination with an orthobiologic. Orthobiologics refer generally to treatment agents that are used to replace, repair, and/or regenerate damaged tissue and/or bones. Orthobiologics include osteoinductives, also known as growth factors, which are a type of orthobiologics that are configured for regenerating bone. Examples of osteoinductives include proteins that activate the formation of new bone. Another type of orthobiologic is osteoconductive bone replacement materials (resorbable or non-resorbable), which assist bone regeneration by providing a scaffold that supports the ingrowth of capillaries and provides a host bed for new cells.

The agent can be applied in a separate step during the procedure or integrated into the device. For example, the balloon 14 can be coated with the agent or the agent can be embedded within the balloon 14. The device 10 can also be configured to deliver the agent as it is deployed. For example, as described above, in one embodiment, the balloon 14 comprises a first, inner layer which restrains the hardenable media. A second, outer layer is coaxially disposed about the first layer, and is provided with a plurality of apertures or a microporous structure. An infusion lumen is provided in the delivery device for providing communication between a proximal infusion port and the space in between the inner and outer balloon layers. In this manner, suitable orthobiologics or bone matrix material such as a hydroxyapatite preparation can be injected into the central lumen and through the perforations to promote bone in-growth and fusion with the adjacent spinal bone material.

Delivery Device

With reference now to FIGS. 4-8, an exemplary embodiment of a deployment system for deploying the inflatable corpectomy device 10 described above will now be described. As shown, the system comprises a delivery catheter 100 which deploys the implantable inflatable orthopedic device 10. The delivery catheter 100 preferably includes an elongate, flexible tubular body 104, having a proximal end 106 and a distal end 108. For certain applications, however, in which direct linear access is intended, the tubular body 104 may be substantially rigid. The tubular body 104 includes one or more passages or lumens extending axially through the body, depending upon the desired functionality of the device.

The overall length and cross sectional dimensions of the delivery catheter 100 may be varied, depending upon the intended clinical application. In a device intended for inserting the device 10 in percutaneous or minimally invasive manner into a space between an upper and lower vertebrae, for example, the tubular body 104 will generally have a length within the range of from about 15 cm to about 50 cm, and a diameter within the range of from about 2 mm to about 6 mm.

Percutaneous insertion of the delivery catheter 100 may be facilitated by the provision of a removable elongate stiffening wire 122, extending through a lumen such as inflation lumen 130 (see FIG. 5) from the proximal end 106 of tubular body 104, to the distal end 108 of tubular body 104. Optionally, the stiffening wire 122 extends into, and even all the way to the distal end 18 of the orthopedic device 10, to provide support and column strength to the device 10, which may be desirable during tissue penetration. The distal end of the stiffening wire 122 may be connected to a coil approximately 8 cm in length to allow for a degree of flexibility.

Figure 5:
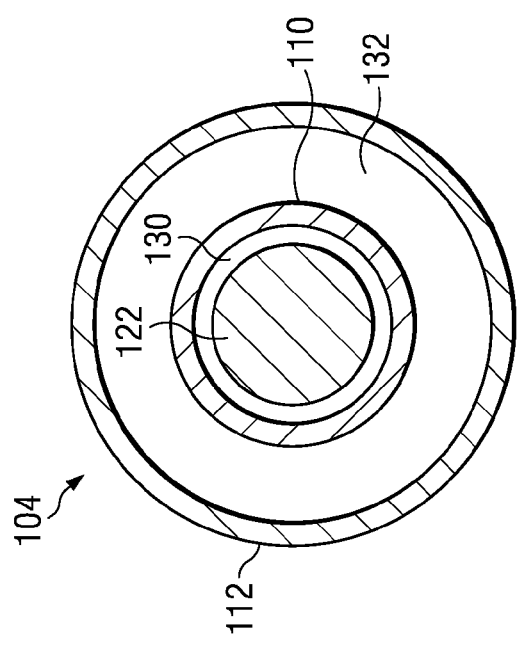
FIG. 5 is a cross-sectional view taken through line 5-5 of FIG. 4.

FIG. 5 shows a cross-sectional view through the elongate body 104, showing (not to scale) an inner sleeve 110 and an outer sleeve 112. The inner sleeve 110 defines a first, inflation lumen 130, while a second, venting lumen 132 is defined by the annular space between the inner sleeve 110 and outer sleeve 112. The inflation lumen 130 is adapted to receive the elongate stiffening wire 122 in a sliding fashion through a proximal opening 127 on inner sleeve 110, which in turn extends axially into the outer sleeve 112 by way of port 126 in catheter manifold 124. Although the illustrated embodiment has a dual lumen, concentric or coaxial configuration, three or more lumen may alternatively be provided, depending upon the desired capabilities of the catheter. A single lumen catheter may also be provided, to accommodate a removable stiffening wire, if utilized, and to facilitate inflation of the implantable device. Alternatively, a two or more lumen catheter shaft may be fabricated, extruded or otherwise formed with the lumen in a side-by-side configuration.

Figure 6:
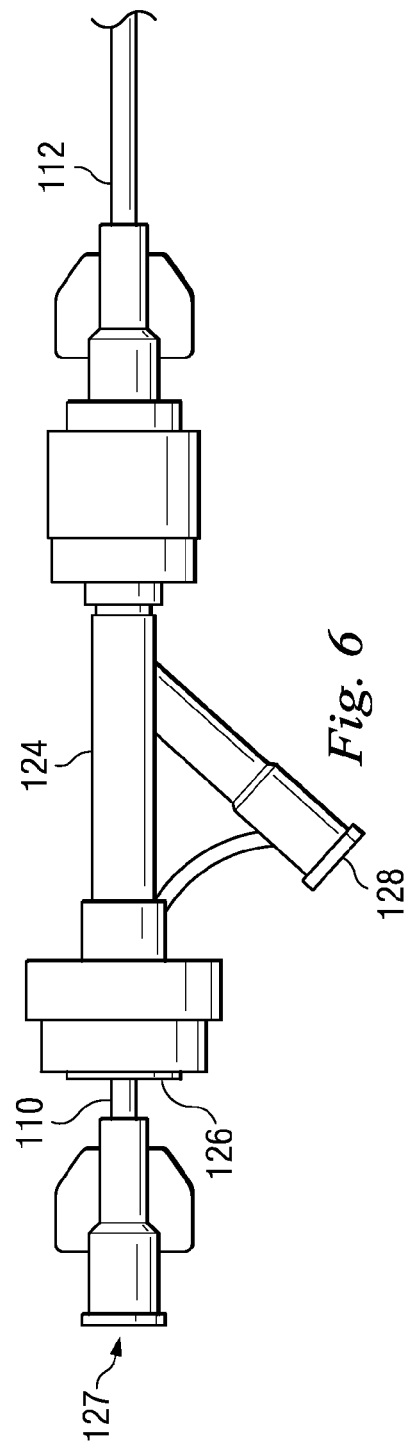
FIG. 6 is an enlarged view of the proximal portion of the delivery catheter shown in FIG. 4.
Figure 7:
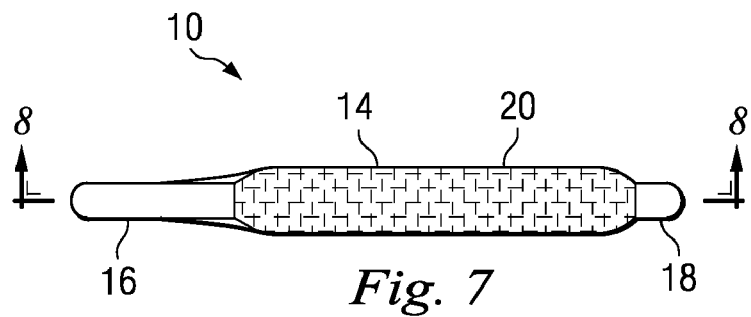
FIG. 7 is a side view of the inflatable corpectomy device of FIG. 4.

With reference to FIGS. 4 and 6, the deployment device 100 further comprises a manifold 124, located at the proximal end 106 of the elongate tubular body 104. The catheter manifold 124 provides a maneuvering handle for the health care professional, and supports an inflation port 126 and a vent port 128. Either or both the inflation port 126 or the vent port 128 may be provided with a coupling, such as a luer-lock fitting for connection to associated devices as is known in the art. For example, a luer or other connector on the inflation port 126 facilitates connection to a source of pressurized inflation media in a conventional manner. The vent port 128 may be connected to a syringe or other device to draw a vacuum, to evacuate air from the balloon prior to infusion of the hardenable media.

The manifold 124 may also include an injection port for allowing injection of radiopaque contrast fluid to enable visualization of the delivery device on a fluoroscope. The proximal manifold 124 may be machined or injection molded of any of a variety of known suitable materials such as PTFE, ABS, nylon, polyethylene, polycarbonate, or others known in the art. A precision gasket may also be provided, which seals securely around the inner sleeve 110, prohibiting fluid loss.

Catheter manufacturing techniques are generally known in the art, including extrusion and coextrusion, coating, adhesives, and molding. The catheter of the present invention is preferably made in a conventional manner. The elongate shaft of the catheter may be extruded, using polymers such as Nylon, PEBAX, PEEK, PTFE, PE or others known in the catheter arts, the stiffness of which may be selected as appropriate. Material selection varies based on the desired characteristics. The joints are preferably bonded. Biocompatible adhesives or heat bonding may be used to bond the joints. The balloon and stent are also made in a conventional manner.

Figure 4B:
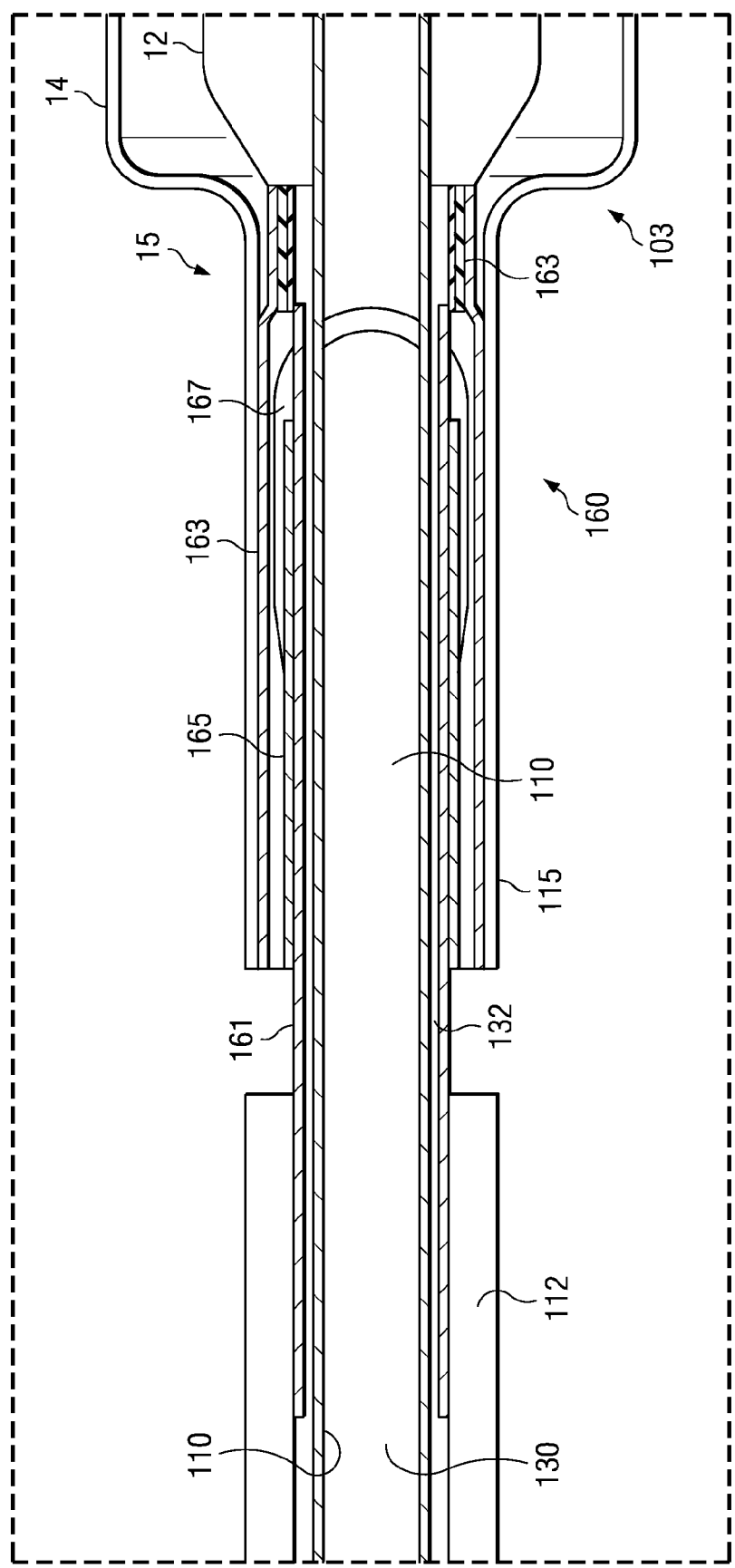
FIG. 4B is an enlarged view of the portion labeled 4B-4B in FIG. 4A.

Referring to FIGS. 4A and 4B, the illustrated elongate tubular body 104 comprises the outer sleeve 112 and the inner sleeve 110 movably positioned within the outer sleeve 112. The inflatable device 10 is removably carried by or near the distal end 108 of the outer sleeve 112. Alternatively, the inflatable device 10 may be removably carried by the inner sleeve 110. The inner sleeve 110 may extend into the inflatable device 10, as illustrated. The inflation lumen 130 is therefore in communication with the interior cavity 12 of the inflatable device 10. The inflation media can thus be infused through the inflation portion 126 (or opening 127) located at the manifold 124 to fill the cavity 12.

The balloon 14 may be removably attached to the tubular body 104 by a slip or friction fit on the distal end 108 of the outer sleeve 112 or on the inner sleeve 110. A variety of alternative releasable attachments may be used between the outer sleeve 112 and/or inner sleeve 110 and the proximal end 16 of the balloon 14, such as threaded engagement, bayonet mounts, quick twist engagements like a luer lock connector, and others known in the art. In each of these embodiments, a first retention surface or structure on the outer sleeve 112 and/or inner sleeve 110 releasably engages a complimentary surface or retention structure on the proximal end 16 of the balloon 14 as will be apparent to those of skill in the art.

The balloon 14 preferably comprises a self-sealing valve 160 which prevents the hardenable media from leaking once the delivery catheter 100 is detached from the balloon 14. Valve 160 is provided for closing the pathway between inflation lumen 130 and inner cavity 12. Valve 160 may be located at the proximal end 16 of inflatable device 10. A variety of different valves may be used as will be recognized by those of skill in the art, such as a slit valve, check valve, duck-billed or flap valve. Alternatively, a stopper may be provided which can be placed within the pathway to prevent leakage.

Figure 9A:
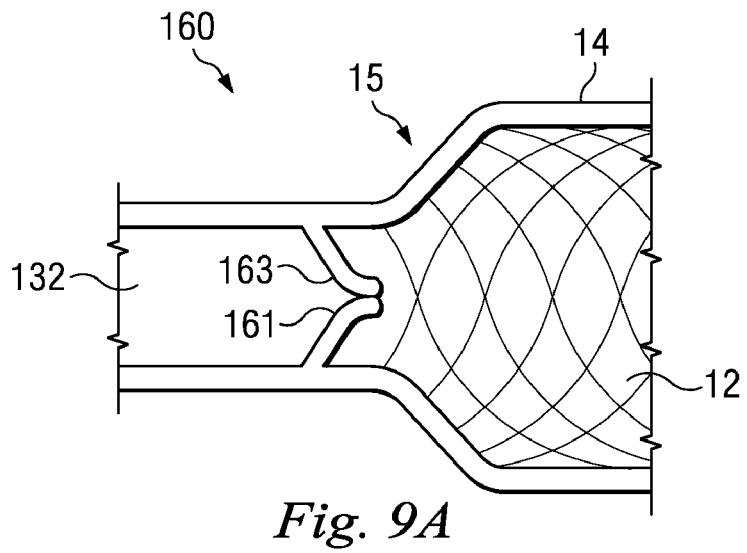
FIG. 9A is a schematic cross-sectional view of a valve of the inflatable device of FIG. 7.

Referring to FIG. 9A, a duck bill valve is schematically illustrated. This valve includes at least a first, and preferably, two or more coaptive leaflets 162 and 163, which incline towards each other in the distal direction as will be understood by those of skill in the art. Distal advancement of the inner sleeve 110 and/or pressurized media through the valve 160 forces the coaptive leaflets 162 and 163 apart, to facilitate introduction of the hardenable media. Upon removal of the inner sleeve 110, the coaptive leaflets 162 and 163 return to a closed configuration to inhibit or prevent the escape of hardenable media. A single leaflet 162 may be utilized, in the form of a flapper valve.

An alternate valve is illustrated in FIGS. 9B and 9C, and in an assembled device in FIG. 4B. In this valve, a tubular support structure 165 is provided with a closeable cap 167. The closeable cap 167 may be formed from any of a variety of highly flexible polymeric materials, such as silicone, neoprene, latex, or others known in the art. Cap 167 may be formed such as by dip molding or liquid injection molding, followed by the provision of a slit or potential opening 169.

The valve 160 may be connected to or formed with the inflatable device 10 in any of a variety of manners, as will be appreciated in view of the disclosure herein. In the illustrated embodiment, the balloon 14 is provided with a proximally extending neck 15 which carries the valve 160 therein. The tubular body 165 having the cap 167 thereon is positioned concentrically within the proximal neck 15, as illustrated in FIG. 4B. Alternatively, the valve 160 may be positioned within the balloon 14, i.e., distally of the proximal shoulder of the balloon 14.

Additional details of one detachable connection between the delivery system and the implantable device is illustrated in FIG. 4B. As illustrated therein, a tube 161 extends distally from the outer sleeve 112. Tube 161 may comprise any of a variety of materials, which exhibit sufficient structural integrity for the intended use. In one embodiment, tube 161 is a metal hypotube having an inside diameter of about 0.085" to about 0.086 and a wall thickness of about 0.001" to about 002". The tube 161 in the illustrative embodiment extends for a distance of about 0.50 mm to about 0.75 mm beyond the distal end of the outer sleeve 112.

The tube 161 extends into a sliding fit with a tubular support structure 163 which may be positioned in a proximal neck portion 15 of the balloon 14. When positioned as illustrated, the tube 161 ensures that the valve 160 is open, so that the inner sleeve 110 may extend axially therethrough into the balloon 14.

In addition, the inside diameter of the tube 161 is preferably sufficiently larger than the outside diameter of the inner sleeve 110 to provide an annular passageway in communication with the vent lumen 132. This structure ensures that the interior 12 of the balloon 14 remains in communication with the proximal vent port by way of a vent lumen 132 extending throughout the length of the assembly. In the illustrated embodiment, the outside diameter of the inner sleeve 110 is about 0.082" to about 0.084", and the inside diameter of the tube 161 is about 0.085" to about 0.086". Following infusion of the curable media into the balloon, the inner tube 110 and tubular body 161 are both proximally retracted from the balloon, thereby enabling the valve 160 to close as is described elsewhere herein.

Figure 8:
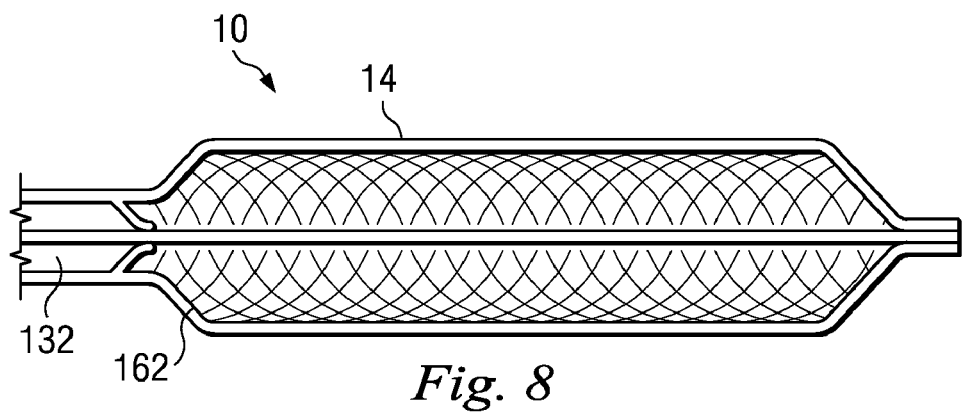
FIG. 8 is a cross-sectional view through of the device of FIG. 7 with the device in an expanded condition.

When fully inflated, as shown in FIG. 8, the balloon 14 has an inflated profile with a cylindrical disk-type shape.

FIG. 10 illustrates the structure of an accelerator for accelerating the curing of the curable media in one embodiment of the invention. In this embodiment, the accelerator comprises a heating coil 300 within the device 10 such as concentrically around the distal end of the inner sleeve 110 of the elongate tubular body 104 of a delivery catheter 100. While the heating coil 300 is shown coiled around the exterior surface of the distal end of the inner sleeve 110, it can also be fitted inside the distal end of the inner sleeve 110, or embedded within the distal end of the inner sleeve 110. The distal portion of the sleeve 110 may be provided with a detachable joint at the proximal end 16 of the balloon 14 such that it is left behind within the implantable device 10 following removal of the delivery catheter 100. A variety of releasable attachments may be used, such as threaded engagements, bayonet mounts, quick twist engagements like luer lock connectors, or others known in the art.

It should be appreciated that the accelerator is not necessary a part of the delivery catheter 100. FIG. 11 schematically illustrates another embodiment in which the accelerator is built into the inflatable orthopedic device 10. As disclosed above, a variety of structures may be provided such as a reinforcement element 120 in the cavity 12 of the balloon 14, such as carbon fibers, titanium rods, or tubular stents. If the reinforcement element 120 is made from electrically conductive materials, it can also function as a resistive heating element. In FIG. 11, a metallic stent is illustrated. Titanium rods and carbon fibers may also be used. Electrical contacts 310 and 312 for conducting a current through the reinforcement element 120 are incorporated into the releasable attachment, such as a concentric sliding fit connection, used between the outer sleeve 112 and/or inner sleeve 110 and the proximal end 16 of the balloon 14. These electrical contacts engage complimentary contacts on the outer sleeve 112 and/or inner sleeve 110 to complete an electric circuit with a proximally located power supply for running the resistive heating element.

In order to accomplish the objective of accelerating polymerization of the epoxy or other hardenable media, the heating element preferably elevates the temperature of the epoxy to a point above normal body temperature. Temperatures at the heating element of at least about 43°, preferably at least about 50°, and, under certain circumstances as high as 60° C. or more are desirable to produce an optimal cure rate. However, the outside of the implant is preferably not heated to the extent that it causes localized tissue necrosis. Tissue necrosis occurs at approximately 45° C. Thus, the heat source preferably sets up a temperature differential between the surface of the implant and the interior of the implant. This may be accomplished in several ways, such as, for example, selecting materials and thickness of the outer flexible wall 20 to provide thermal insulation of the adjacent tissue from heat generated by the heating element. As an alternative or in addition, heat sink structures may be provided at or near the outer surface of the orthopedic device 10. A flow path such as an annular space formed within a double walled balloon may be utilized to circulate a coolant such as saline or other circulating cooling fluid. Such measures preferably permit the heating element to be heated as high as 50° C. or higher, while maintaining the outside surface of the device 10 at a temperature of no more than about 45° C., and, preferably no more than about 43° C.

Excessive temperature can also be reached transiently, such as at the beginning of a heating cycle when the temperature may temporarily overshoot the 45° C. desired maximum. In certain embodiments, the initial temperature overshoot can be eliminated or reduced by appropriately driving the power to the heating element as is discussed in detail below. The driver circuitry preferably brings the heating element up to operating temperature rapidly, while minimizing the risk of thermal overshoot beyond a predetermined maximum. All of the foregoing measures preferably allow a sufficient curing of the hardenable media to limit the required period of immobility to no more than about 2 hours, preferably no more than about 1 hour and, optimally no more than about 45 minutes post implantation. Although a complete cure is not required within this time window, a sufficient cure is desirable that the patient need not be immobilized beyond the initial cure. Thereafter, the hardenable media will continue to harden, such as over the next few hours or even days, but with little or no restriction on the patient's activities.

The resistive heating element, whether the heating coil 300, the reinforcement element 120, or other structure, may be made from material with either a positive or negative temperature coefficient of resistance, e.g., electrical resistance either directly or indirectly proportionate to temperature, respectively. The temperature may be monitored by measuring the DC voltage across the resistive heating element, for the voltage is directly proportional to resistance for a given current, and the temperature coefficient of resistance is known. Alternatively, by measuring the voltage, current and phase of the drive system, the resistance of the heating element and thus its temperature can be calculated by a microprocessor or dedicated circuitry.

Alternatively a thermistor 314 may be used to monitor the temperature of the device 10. Thermistors are well known in the art. Using one or more separate thermistors 314 would entail more electrical contacts (not shown) as another electrical loop in addition to the one running the heating element may be necessary. Other methods of measuring the temperature include the use of an optical fiber in conjunction with a thermally reactive material, a coaxial plunger in conjunction with a thermal bulb, or a semiconductor temperature sensor or junction (such as a diode) carried by the orthopedic implant. A bimetallic heating element may function similarly to a circuit breaker and self-regulate.

Additional details and embodiments of an accelerator for the device 10 can be found in U.S. Pat. No. 6,875,212, which has been incorporated by reference into this application.

In the embodiments described above, a valve and/or a detachable connection is provided between the device 10 and the deployment catheter 100. FIG. 12 illustrates an embodiment in which the device 10 and inflation lumen 130 are semi-permanently or permanently coupled together. Intone embodiment, the inner sheath 110 is coupled to the proximal end 16 of the balloon 14 by a heat bond or adhesive. In another embodiment, the balloon 14 is shrink-fitted onto the sheath 110. This places inflation lumen 130 of the catheter 100 in fluid communication with the cavity 12 of the balloon 14. In another embodiment, the balloon 14 is integrally formed with at least a portion of the catheter 100 which defines the inflation lumen 130. In such an embodiment, the device 10 is detached from the catheter 100 by physically separating by cutting or otherwise separating the balloon 14 from the catheter 100. Preferably, this is done after the hardenable material is sufficiently cured such that separation from the catheter will not cause the balloon 14 to deflate.

Methods of Use

Although the application of the present invention will be disclosed in connection with corpectomy, the methods and structures disclosed herein are intended for various other spinal and applications, as will be apparent to those of skill in the art in view of the disclosure herein. In addition, although the method is described in the context of a single level fusion procedure in which a single vertebral body or portion thereof is removed, the method can also be extended to multiple level fusion procedures.

In one embodiment, the method generally involves accessing the diseased or damaged parts of a vertebrae bone. The diseased or damaged parts are then removed using techniques and tools that are well known in the art. The removal step can utilize open, minimally open or percutaneous techniques. An inflatable corpectomy device, as described above, is then inserted, preferably percutaneously, into the space formerly occupied by the removed or damaged vertebrae bone or portions thereof. The corpectomy device repositions or fixes the vertebrae below and above the replaced vertebra, to a position within the vertebral column which is more stable or which causes less morbidity.

Referring now to FIG. 13 through FIG. 18, there are shown a series of drawings depicting various stages of an embodiment of a method of replacing diseased or damaged vertebra or a portion thereof. FIGS. 13-18 show partial cutaway, perspective, midline sagittal views of a portion of a vertebral column undergoing the method.

Figure 13:
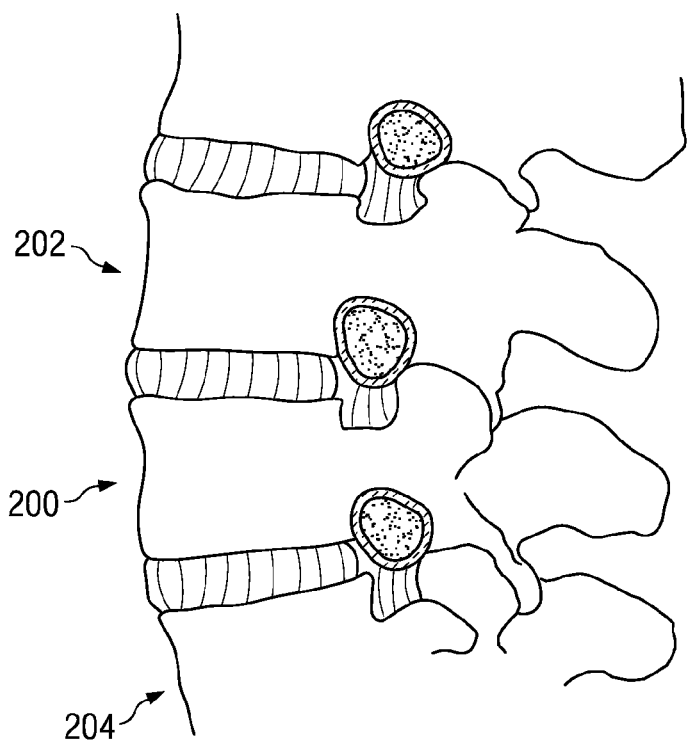

The method will now be disclosed and depicted with reference to only one vertebrae, one of which is either diseased, damaged or in need of replacement or repair. As shown in FIG. 13, the targeted vertebrae bone 200 is positioned between two (upper and lower) generally healthy vertebral bones, 202, 204. However, the method can also be applied to two or more damaged vertebrae simultaneously, as will be understood by those with skill in the art with reference to this disclosure. Additionally, the method can be used to replace the L5 vertebrae, using the cranial-ward portion of the sacrum as the "vertebrae" with which L5 is anchored. It is also possible to remove and replace only a portion of the damaged vertebrae bone 200.

The present method comprises identifying a patient who is a suitable candidate for undergoing the method. In connection with a spinal application, a suitable candidate has one or more damaged or diseased vertebrae. Further, the suitable candidate will normally have either pain, loss of function or real or potential instability which is likely due to the portions of the diseased or damaged vertebrae that blocks or pinches the spinal cord. For example, a suitable patient can have a disease or condition such as a tumor, spondylosis, spondylolisthesis, vertebral instability, spinal stenosis and degenerated, herniated, or degenerated and herniated intervertebral discs, though actual indications require the expertise of one of skill in the art as will be understood by those with skill in the art with reference to this disclosure.

Next, the present method comprises making a stab incision in the patient's skin overlying the patient's vertebral column at or near the level of the vertebrae or portion of vertebrae to be repositioned or fixed. In one embodiment, the incision is made posteriorly at or near the level of the pedicle of the vertebra or portion of vertebra to be replaced. The pedicle level is located preferably by identifying the pedicle shadow using fluoroscopy. While a posterior approached is described, those of skill of the art will recognize an anterior, posterior and/or lateral approaches or combinations thereof can also be used.

Figure 14:
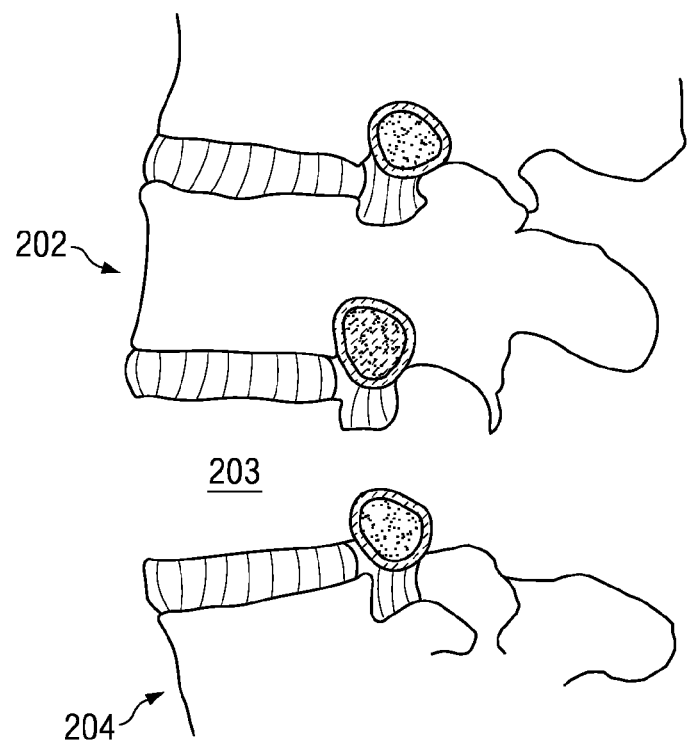

Then, as shown in FIG. 14, after the incision is made, the diseased and damaged portions of the vertebrae bone are removed to relieve pressure from the spinal cord. The removed bone forms a gap 203 positioned generally between the upper and lower vertebrae bones 204, 202. Various techniques and devices (e.g., bone burrs and cutters) can be used to remove the diseased and damaged bone 200 or portions thereof using either open, minimally open or percutaneous techniques. In that corpectomy is a well-known procedure, a detailed description of such devices and techniques is not necessary.

As shown in FIG. 15, the disc levels below and above the removed vertebral body can then be removed along with any vertebrae fragments. The bone surfaces of the upper and lower vertebrae bones 202, 204 are then cleared and prepared to receive the inflatable device. With continued reference to FIG. 15, bolts or screws 210 can be inserted into the upper and lower vertebrae bones 202, 204 to help surgeon maintain or manipulate the position of the upper and lower vertebrae 202, 204 and the size of the gap 203.

Figure 19:
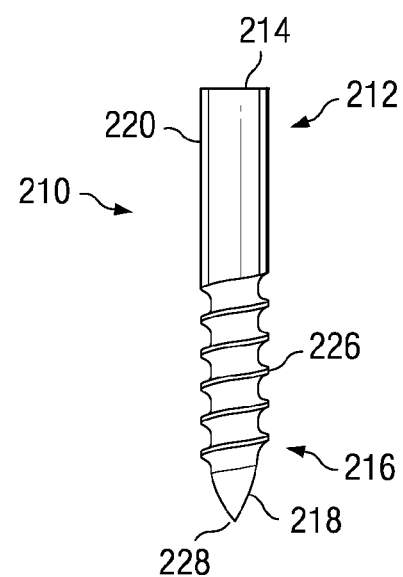
FIG. 19 is a side elevational view of a bone screw or bolt.

With reference to FIG. 19, the screws or bone anchors 210 can be made a biocompatible material such as titanium or stainless steel. Alternatively, bone anchors 210 may be made of a composite material. Bone anchors 210 may also be made of a suitable medical grade polymer.

The bone anchor 210 comprises a proximal portion 212 having a proximal end 214 and a distal portion 216 having a distal end 218. The proximal portion 212 typically comprises a head 220 for engaging various gripping tools and plates. In a preferred embodiment, the head 220 is also configured to mate with a driving device, such as, tip of a screwdriver. The head 220 may comprise a standard or Phillips slot for mating with the screwdriver. A variety of slot configurations are also suitable, such as hexagonal, Torx, rectangular, triangular, curved, or any other suitable shape.

The distal portion 216 of bone anchor 210 typically comprises threads 226 and a distal end 218 having a sharp tip. The bone anchor 210 can include a central lumen (not shown) extending coaxially completely through bone anchor 210 from proximal end 214 to distal end 218 and configured to receive a guidewire. The bone anchor 210 may also include at least one or more perforations to permits bone to grow into bone anchor 210, stabilizing bone anchor 10 within the bone. Additionally, bone matrix material such as a hydroxyapatite preparation can be injected into the central lumen and through the perforation to promote bone in-growth.

With reference now to FIG. 16, while the vertebral space 203 is open, the un-inflated or partially inflated device 10 is positioned in the space 203 between the upper and lower vertebral bodies 202, 204. In the illustrated embodiment, the device 10 is inserted with the deployment catheter 100 using a posterior approach. However, the catheter 100 and the device 10 can be inserted using an anterior or lateral approach. In addition, although percutaneous techniques are preferred, the device can also be inserted using open on minimally open procedures. In one embodiment, the device 10 is percutaneously inserted into the space 203 using a transpedicle approach in which a deployment catheter is advanced through a pedicle 230 of adjacent vertebrae 202, 204.

If a percutaneous method is used, a guidewire can be advanced through the patient's tissue or bone and into the space 203 between the upper and lower vertebral bodies 202, 204. Then, the entire guidewire tract or portions thereof can be dilated using a high pressure balloon or another type of expandable device and a flexible introducer sheath may be passed over the guidewire along the entire guidewire tract. The guidewire is removed after the introducer sheath is placed. Alternatively, the device 10 is advanced over the wire using the catheter 100 without the use of a sheath.

Figure 17:
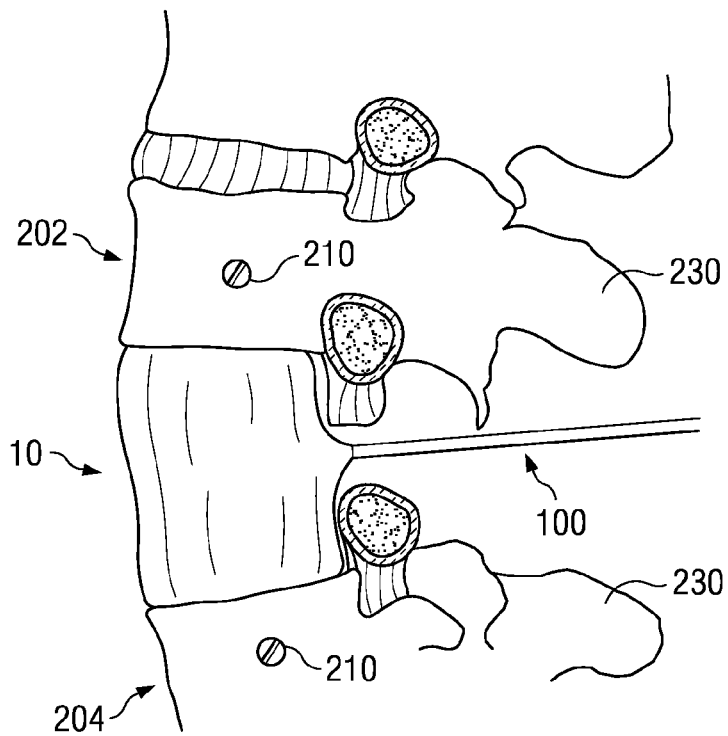

Then, as shown in FIG. 17, the device is inflated with a rapid setting, liquid polymer, or its equivalent, and the polymer is allowed to fix the space formerly occupied by the damaged vertebrae bone. In one embodiment, the liquid polymer is or includes a two part epoxy or other hardenable media such as those discussed elsewhere herein, and curing is accelerated by the application of heat. Preferably, as the device is hardening, the upper and lower vertebrae are maintained in the desired position by the surgeon using the fixation devices 210. As mentioned above, the device 10 can used in combination with the treatment agents that are used to promote fusion, replace, repair, and/or regenerate damaged tissue and/or bones.

Figure 17A:
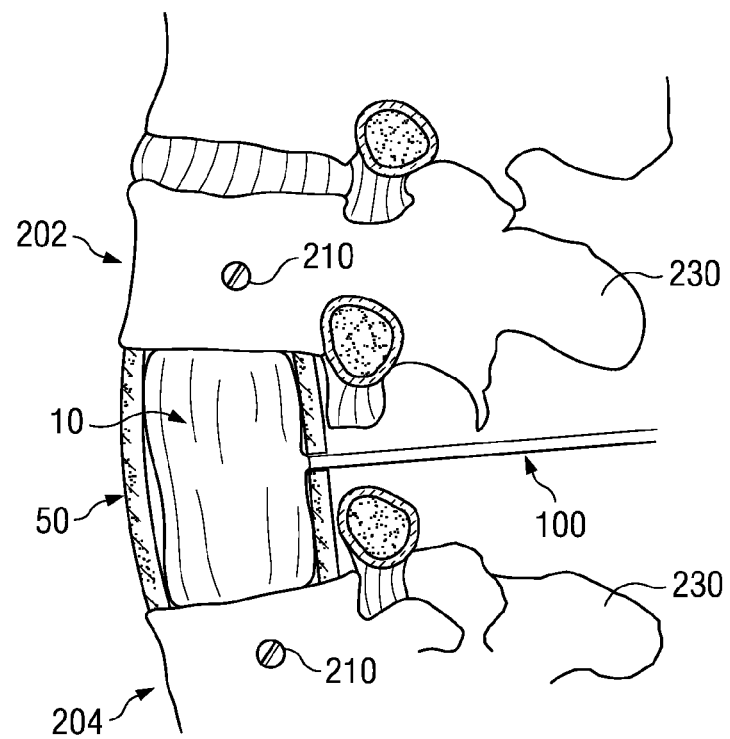

FIG. 17A illustrates an embodiment in which the device 10 is used in combination with a bone graft 50. In such an embodiment, the bone graft 50 can be inserted into the space between the upper and lower vertebrae bones 202, 204. The inflatable device 10 can then be inserted through an opening 56, which is preformed or formed in situ, and inflated to fill the bore 54 within the graft 50.

Figure 18:
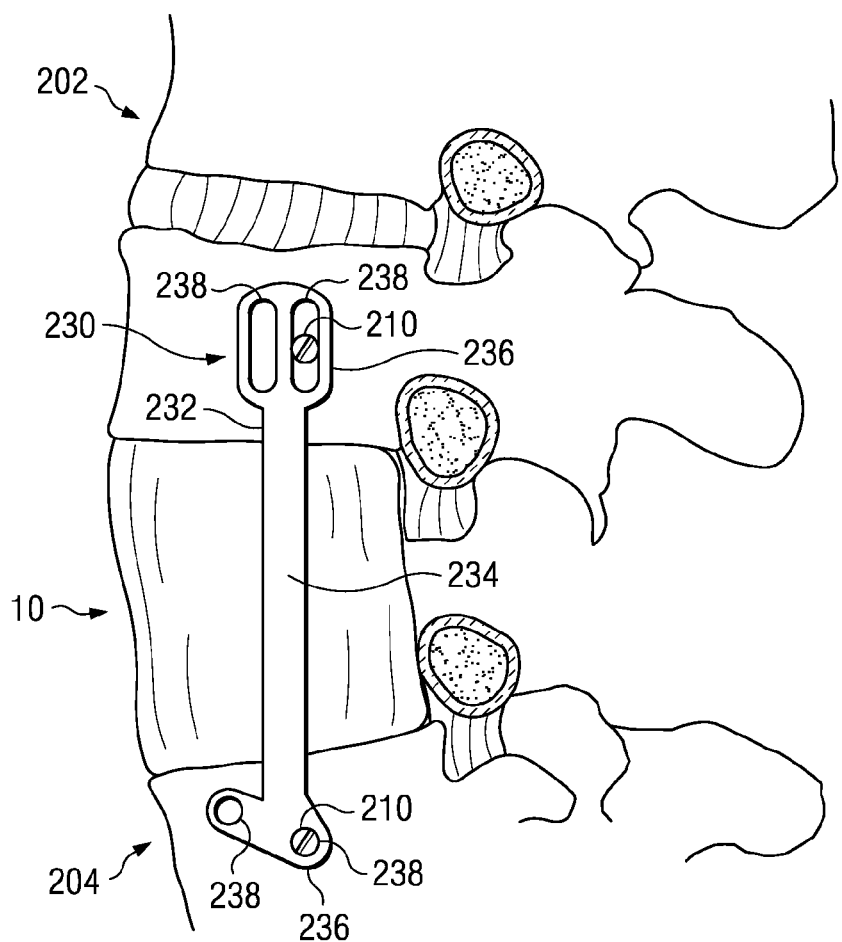

Finally, as shown FIG. 18, the delivery or pushing catheter 100 is separated from the device 10 by pulling on the catheter 100. As mentioned above, the inflatable device 10 can comprise a self-sealing valve which prevents the polymer from leaking once the pushing catheter 100 is detached. In a modified embodiment, as described above, with reference to FIG. 12, the device 10 does not include a self sealing valve but is instead separated from the balloon 14 by, for example, cutting the balloon 14 from the inflation lumen 130, after the inflation material has sufficiently cured.

As shown, in FIG. 18, the inflated device 10 closes the vertebral space and is secured tightly between the upper and lower vertebral bones 204, 202. FIG. 18 also illustrates the use of a support structure 230 that bridges the upper and lower vertebral bodies 204, 202, providing support while the device 10 or graft 50 fuses to the upper and lower vertebral bones 204, 202. In the illustrated embodiment, a plate 232, often referred to as a Z-plate, is provided between the upper and lower vertebral bodies 204, 202. The plate 232 generally includes an elongated rod 234 that bridges the two bodies and flanges 236 at the ends of the rod 234. The flanges 236 include openings 238 for receiving the fixation devices 210 and additional anchoring elements if desired. The plate 232 keeps the area secure while the area heals. Over time, the bone graft 50 or device 10 will knit with the upper and lower vertebral levels to create a solid bone segment.

With the procedure completed, the access incisions are closed or sealed as necessary and routine postoperative care administered.

In one embodiment, there is provided a kit for performing methods of the present invention. The kit comprises a plurality of bone screws and/or plates as described above for attachment to the upper and lower vertebrae. The kit can also comprise other components of a system according to one of the embodiments described above, such as a guidewire, an inflatable corpectomy device, the components of the polymer system to be mixed and injected and/or a delivery catheter. In another preferred embodiment, the kit also comprises inflatable corpectomy devices of several sizes to accommodate different anatomies and patients.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A method of implanting a corpectomy device comprising:
   providing a balloon having an inflated configuration sized to fill a space between a first vertebra and a non-adjacent second vertebra and a deflated configuration sized for minimally invasive insertion into the space between the first and second vertebrae;
   providing a hardenable media for introduction into the balloon;
   performing a minimally-invasive corpectomy procedure on a third vertebra positioned between the first and second vertebrae to create the space between the first and second vertebrae;
   introducing the balloon in the deflated configuration into the space between the first and second vertebrae via a minimally invasive approach;
   inserting the hardenable media into the balloon to inflate the balloon to the inflated configuration via a minimally invasive approach;
   hardening the hardenable media within the balloon to form a rigid support structure between the first and second vertebrae to stabilize the first and second vertebrae; and
   inserting a bone graft into the space;
   wherein introducing the balloon into the space comprises inserting the balloon into the bone graft.

2. The method of claim 1, further comprising:
   attaching an elongated support structure to the first vertebra and the second vertebra such that the support structure extends between the first and second vertebrae.

3. The method of claim 1, wherein the hardenable media has a modulus of elasticity between about 10-200 GPa after hardening.

4. The method of claim 1, wherein the balloon has a height between about 20-40 millimeters in the inflated configuration.

5. The method of claim 1, wherein the balloon has a length between about 20-40 millimeters in the inflated configuration.

6. The method of claim 1, wherein the balloon comprises a self-sealing valve for receiving the hardenable media and wherein inserting the hardenable media into the balloon comprises inserting the hardenable media through the self-sealing valve.

7. The method of claim 1, wherein the balloon comprises a reinforcement element.

8. The method of claim 7, wherein the reinforcement element comprises a resistive heating element.

9. The method of claim 1, wherein the balloon comprises a heating element.

10. The method of claim 9, wherein hardening the hardenable media comprises heating the hardenable media with the heating element.

11. The method of claim 1, wherein hardening the hardenable media comprises heating the hardenable media to a temperature of at least about 50° C. while maintaining an outer surface of the balloon at a temperature less than about 45° C.

* * * * *